United States Patent [19]

Laver

[11] Patent Number: Plant 5,851

[45] Date of Patent: Jan. 13, 1987

[54] ROSE PLANT NAMED LAVBLUE

[75] Inventor: Keith G. Laver, Mississauga, Canada

[73] Assignee: Nor'East Miniature Roses, Inc., Rowley, Mass.

[21] Appl. No.: 682,261

[22] Filed: Dec. 17, 1984

[51] Int. Cl.[4] ..... A01H 5/00

[52] U.S. Cl. ..... Plt./10

[58] Field of Search ..... Plt./10

*Primary Examiner*—R. E. Bagwill

*Attorney, Agent, or Firm*—Vincent G. Gioia

[57] ABSTRACT

A new miniature rose variety of bright currant red flower coloring.

1 Drawing Figure

1

The present invention relates to a new and distinct variety of rose plant of the miniature rose class, which was originated by my crossing as seed parent the rose known as "Dwarfking 78" and as pollen parent the rose known as "Hokey Pokey". The varietal denomination of this new variety is "Lavblue".

Among the novel characteristics possessed by this new variety which distinguish it from its parents and all other varieties of which I am aware are its bright currant red flowers and unusually heavy petalage and which maintain their color and form. Flowers are long lasting on the plant and as cut flowers. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "46A" is plate 46A of The Royal Horticultural Society Colour Chart.

Parentage: Seedling.

*Seed parent.*—"Dwarfking 78".

*Pollen parent.*—"Hokey Pokey".

Class: Miniature.

The following observations are made of specimens grown outdoors in Essex County, Mass., during the month of August.

FLOWER

Blooming habit: Near continuous.

A. Bud:

(1) *Size.*—Medium to small.

(2) *Form.*—Ovoid.

(3) *Color.*—When sepals first divide — dark red near 46A. When petals begin to unfurl — near 46B.

(4) *Sepals.*—Longer than bud, slightly foliated.

(5) *Peduncle.*—Length — about 1¼ to 2". Aspect — straight. Strength — erect. Color — near 138C.

2

B. Bloom:

(1) *Size.*—Average size when fully expanded — about 1½ inches.

(2) *Borne.*—Singly.

(3) *Form.*—Cupped, then very full. High centered, becoming flat outer petals reflex sharply and roll under upon opening.

(4) *Petalage.*—Number of petals under normal conditions — about 50 to 60.

(5) *Color.*—After sepals fall, visible flower coloring is near currant red 46A with very little color difference at petal top and undersurface. Color is stable and constant at near 44A through 44C with darker tones appearing at petal extremities. General tonality from a distance is similar bright red coloring. Color at point of petal attachment is near 8D.

C. Petals:

(1) *Texture.*—Thick.

(2) *Appearance.*—Inside — velvety, outside — velvety.

(3) *Form.*—Broad, fan shaped with pronounced apex on many petals.

(4) *Arrangement.*—Regularly arranged, imbricated.

(5) *Petaloids in center.*—Few.

(6) *Persistence.*—Hang on.

(7) *Fragrance.*—Slight.

(8) *Lasting quality.*—Long lasting on plant and long lasting as cut flower.

REPRODUCTIVE ORGANS

A. Stamens, filaments and anthers:

(1) *Arrangement.*—Irregular.

(2) *Color.*—Near 14C.

B. Pollen:

*Color.*—near 14A.

C. Styles: Uneven length.

D. Stigmas:

*Color.*—Near 150C.

E. Hips: Globular, about 1 inch, orange, seeds protrude.

PLANT

A. Form: Compact, upright, uniform bunching.

B. Growth: Vigorous.

*Height attained.*—about 12 to 15 inches.

C. Foliage: Compound 5 to 7 leaflets.

(1) *Size.*—Medium.

(2) *Quantity.*—Abundant.

(3) *Color.*—New foliage: Upper side — near to 141B with slight near 59C edge. Under side — near to 148C. Old foliage: Upper side — near 136B. Under side — near 148B.

(4) *Shape.*—Oval.

(5) *Texture.*—Upper side is waxy and under side is matte (with veining).

(6) *Edge.*—Serrated.

(7) *Serration.*—Serrulate.

(8) *Leaf stem.*—Color — near 141C. Under side — near 141C.

(9) *Stipules.*—Slightly bearded.

(10) *Resistance to disease.*—Blackspot — average. Mildew — average. Rust — average.

D. Wood:

(1) *New wood.*—Color — near 144B. Bark — smooth.

(2) *Old wood.*—Color — near 144A. Bark — smooth.

E. Thorns:

(1) *Thorns.*—Quantity (mean stalk) — ordinary. On laterals from stalk — few. Form — flat base. Length — small. Color — near 165C. Position — ordinary.

(2) *Prickles.*—Some.

F. Winter hardiness: Requires ordinary protection in extreme climates.

I claim:

1. A new and distinct variety of rose plant of the miniature rose class, substantially as shown and described, characterized particularly by heavily petaled bright red flowers that hold color well through development and aging.

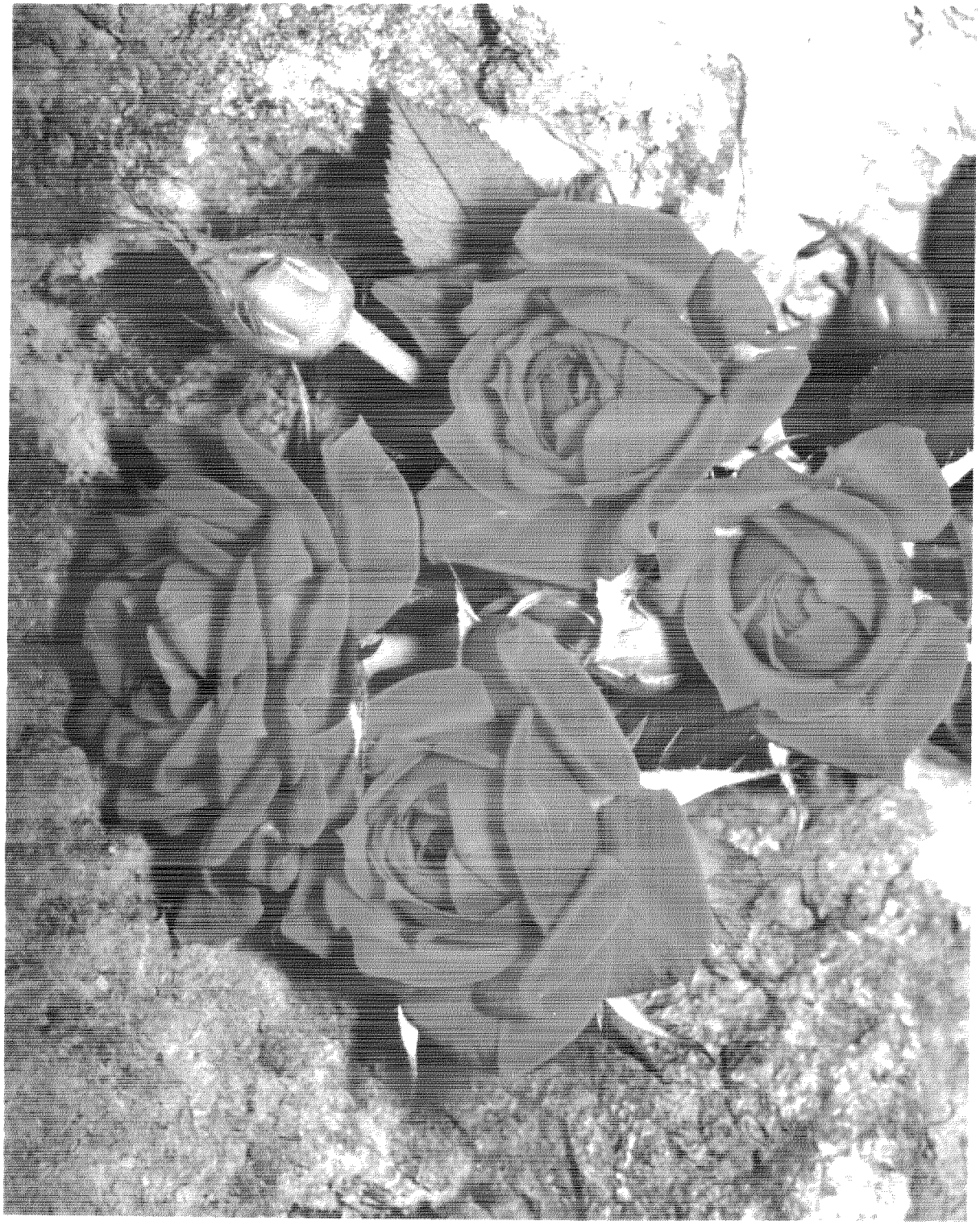

* * * * *